US011660261B2

(12) United States Patent
Lin et al.

(10) Patent No.: US 11,660,261 B2
(45) Date of Patent: May 30, 2023

(54) HIGH VISCOSITY GEL CLEANSING COMPOSITIONS

(71) Applicant: L'OREAL, Paris (FR)

(72) Inventors: Hungta Lin, Teaneck, NJ (US); Ryuji Hara, Springfield, NJ (US); Siliu Tan, Westfield, NJ (US)

(73) Assignee: L'OREAL, Paris (FR)

( * ) Notice: Subject to any disclaimer, the term of this patent is extended or adjusted under 35 U.S.C. 154(b) by 93 days.

(21) Appl. No.: 17/107,340

(22) Filed: Nov. 30, 2020

(65) Prior Publication Data

US 2022/0168199 A1 Jun. 2, 2022

(51) Int. Cl.

| | | |
|---|---|---|
| *C11D 17/00* | (2006.01) | |
| *A61K 8/46* | (2006.01) | |
| *A61K 8/92* | (2006.01) | |
| *A61K 8/04* | (2006.01) | |
| *A61K 8/60* | (2006.01) | |
| *A61K 8/44* | (2006.01) | |
| *A61K 8/9794* | (2017.01) | |
| *A61K 8/20* | (2006.01) | |
| *A61K 8/34* | (2006.01) | |
| *A61K 8/19* | (2006.01) | |
| *A61K 8/36* | (2006.01) | |
| *A61K 8/35* | (2006.01) | |
| *A61Q 1/14* | (2006.01) | |
| *A61K 8/81* | (2006.01) | |

(52) U.S. Cl.
CPC .............. *A61K 8/466* (2013.01); *A61K 8/042* (2013.01); *A61K 8/19* (2013.01); *A61K 8/20* (2013.01); *A61K 8/345* (2013.01); *A61K 8/35* (2013.01); *A61K 8/361* (2013.01); *A61K 8/442* (2013.01); *A61K 8/602* (2013.01); *A61K 8/604* (2013.01); *A61K 8/8147* (2013.01); *A61K 8/922* (2013.01); *A61K 8/9794* (2017.08); *A61Q 1/14* (2013.01); *A61K 2800/30* (2013.01); *A61K 2800/48* (2013.01)

(58) Field of Classification Search
CPC ...... A61K 8/466; A61K 8/8147; A61K 8/042; A61K 8/92; A61K 2800/30; A61K 2800/48
USPC ......................................................... 510/136
See application file for complete search history.

(56) References Cited

U.S. PATENT DOCUMENTS

| | | | |
|---|---|---|---|
| 2013/0072451 A1 | 3/2013 | Lu et al. | |
| 2016/0235639 A1* | 8/2016 | Mathonneau | ............ A61Q 5/02 |
| 2016/0235643 A1* | 8/2016 | Mathonneau | ............ A61K 8/44 |
| 2017/0333324 A1* | 11/2017 | Lalleman | ................. A61K 8/58 |
| 2017/0340540 A1* | 11/2017 | Darras | .................... A61Q 19/10 |
| 2017/0360680 A1* | 12/2017 | Fevola | ..................... A61K 8/732 |
| 2018/0177708 A1* | 6/2018 | Lee | ........................... A61Q 5/02 |
| 2020/0281843 A1 | 9/2020 | Comeron et al. | |

FOREIGN PATENT DOCUMENTS

| | | |
|---|---|---|
| EP | 0870785 A1 | 10/1998 |
| EP | 1120102 B2 | 8/2001 |
| EP | 2611412 B1 | 8/2014 |
| EP | 3260111 A1 | 12/2017 |
| FR | 2861987 A1 | 5/2005 |
| FR | 3030232 A1 | 6/2016 |
| WO | 2014098268 A1 | 6/2014 |
| WO | 2015095870 A1 | 6/2015 |
| WO | 2016145561 A1 | 9/2016 |

OTHER PUBLICATIONS

Unknown, "Technical Data Sheet Aqupec Ser W-150C(CT-1), W-300C(CT-1)" Sumitomo Seika, pp. 1-4, Jan. 1, 2009, XP055616246, https://www.brenntag.com/media/documents/bsi/product_data_sheets/life_science/sumitomo/aqupec_ser_w_150c_pds.pdf.
Benderly et al. "Beyond Thickening—User of Alkyl Acrylate Crosspolymer in Personal Care Formulations" ACS Symposium Series, Washingotn, DC, US, vol. 1148, Aug. 1, 2012, pp. 205-217, XP002792615, European Patent Organization.
Search Report issued to French counterpart Application No. FR 2101242 dated Nov. 12, 2021.
Search Report issued to French counterpart Application No. FR2101170 dated Oct. 28, 2021.
PCT Notification of Transmittal of the International Search Report and the Written Opinion of the International Searching Authority, or the Declaration issued to counterpart Application No. PCT/US2021/061103 dated Mar. 17, 2022.

* cited by examiner

*Primary Examiner* — Eisa B Elhilo
(74) *Attorney, Agent, or Firm* — McNees Wallace & Nurick LLC

(57) ABSTRACT

A cleansing composition includes at least one polymeric thickener having a high electrolyte property and at least one anionic surfactant. The cleansing composition is a gel having a viscosity greater than 25,000 cps. In some embodiments, the cleansing composition is essentially free of sulfates and is essentially free of emulsifiers. In some embodiments, the at least one anionic surfactant includes at least one anionic sulfate surfactant, and the cleansing composition is essentially free of salt.

15 Claims, No Drawings

HIGH VISCOSITY GEL CLEANSING COMPOSITIONS

FIELD OF TECHNOLOGY

The present disclosure is directed to cleansing compositions. More specifically, the present disclosure is directed to high viscosity gel skin cleanser and make-up removal cleansing compositions and systems including a polymeric thickener and an anionic surfactant.

BACKGROUND

Consumers of cosmetic cleansing compositions seek products that have pleasing aesthetic properties. There are several examples in the art that describe products that have desirable properties including viscosities that are designed to enhance the feel of the product while providing suitable emollient and cleansing properties. In one example, U.S. Patent Application No. 2013/0072451 discloses 0.01% to about 5% of an acrylic polymer. The composition has a viscosity of from about 80 to about 1000 mPa·s and a pH of from about 4 to about 9. The acrylic polymer provide a selection yield value of at least 0.11 Pa. In another example, WO 2016/145561 discloses stable low-viscosity oil-in-water emulsions including crosslinked polymeric gelling agents, such as carbomers, including non-alkyl-modified carbomers and alkyl-modified carbomers, such as acrylates/C10-30 alkyl acrylate crosspolymer. In yet another example, EP2611412B1 discloses a hair fixative gel including crosslinked acrylic copolymers functions both as a fixative/film former and a thickening agent for hair. In yet another example, WO 2015/095870 discloses fixative polymers and the use of these polymers in hair styling compositions. In yet another example, EP0870785A1 discloses crosslinked acrylic copolymers obtainable by copolymerization of a monomeric system. The crosslinked acrylic copolymers provide thickening and suspending in aqueous emulsions.

Conventional surfactant cleansers without an emulsifier only include up to 1 oil. Conventional surfactant cleansers with an emulsifier only include up to 20% oil. Stability is also an issue for conventional surfactant cleansers containing high amounts of oil.

Conventional shampoo cleansing compositions include silicone to aid in combability but can only contain about 0.5 wt % to 1 wt % silicone, because the addition of silicone decreases the viscosity of the shampoo.

There is a need for cleansing compositions that provide the desired thickness and other aesthetic properties that consumers seek while providing the emollient and cleansing benefits.

BRIEF SUMMARY

In an exemplary embodiment, a cleansing composition includes at least one polymeric thickener having a high electrolyte property and at least one anionic surfactant that is not a sulfate. The cleansing composition is essentially free of emulsifiers. The cleansing composition is a gel having a viscosity greater than 25,000 cps.

In another exemplary embodiment, a cleansing composition includes at least one polymeric thickener having a high electrolyte property and at least one anionic sulfate surfactant. The cleansing composition is essentially free of salt. The cleansing composition is a gel having a viscosity greater than 25,000 cps.

Other features and advantages of the present disclosure will be apparent from the following more detailed description of the preferred embodiment which illustrates, by way of example, the principles of the disclosure.

DETAILED DESCRIPTION

According to the disclosure, a gel cleansing composition is provided that includes a polymeric thickener and an anionic surfactant.

The gel cleansing composition has a surprising and unexpected stability, high foam production and high viscosity, even in the presence of up to about 40 wt % oil.

The high-foaming, high-viscosity gel cleansing composition provides the surprising and unexpected benefit of a light, fresh feeling with a gel-like texture when applied to skin, different from conventional cleansing compositions that include a polymeric thickener.

In some embodiments, a low concentration of a polymeric thickener of an acrylates crosslinking copolymer with electrolytic properties in combination with an anionic surfactant provides an unexpected high viscosity gel having a firm structure in a cleansing composition. As used herein, high viscosity refers to a viscosity greater than about that is at or greater than at least about 10,000 centipoise (cps). Thus, in various embodiments, the cleansing composition has a viscosity of at least 10,000 cps, or at least 15,000 cps, or at least 20,000 cps, or at least 25,000 cps, or at least 30,000 cps, or at least 40,000 cps, or at least 50,000 cps, or any value, range, or sub-range therebetween.

As used herein, the term "stability," with respect to a cleansing composition, refers to the cleansing composition remaining in a mixed high-viscosity state and not separating, such as not phase separating. Such properties may be achieved even with the inclusion of high amounts of oils, which typically change the surface tension and reduce or prevent foaming of a composition. In some embodiments, a cleansing composition has a high viscosity while also containing a high concentration of oils, which tend to reduce the viscosity of a composition. Such properties may be achieved even with the inclusion of high amounts of silicones. In some embodiments, a cleansing composition has a high viscosity while also containing a high concentration of silicones, which tend to reduce the viscosity of a composition.

Stability is evidenced by one or both of direct measurement of viscosity or visual inspection. For purposes hereof, a composition that demonstrates physical stability and does not become loose or flowing, as evidenced by visual inspection, is stable. In various embodiments, an inventive composition remains stable at temperatures in the range from about 5° C. to about 45° C., over a time period of at least two months, or at least three months, or at least four months, or at least six months, or any value, range, or sub-range therebetween. In some embodiments, a cleansing composition is stable at 25° C. for at least three months, or at least four months, or at least six months, or at least nine months, or at least 12 months, or any value, range, or sub-range therebetween. In some embodiments, a cleansing composition is stable at 45° C. for at least one month, or at least two months, or at least three months, or at least four months, or at least six months, or any value, range, or sub-range therebetween. As disclosed and exemplified herein, a cleansing composition is stable at 45° C. for at least about three months or more.

As used herein with respect to the foaming property of cleansing formulations, including the inventive cleansing composition, the term "Foaming Capacity" means and refers to the capacity of a composition (inventive or comparative) to develop a foam upon rubbing or agitation that would be associated with applying and gently scrubbing skin or other keratinous substrates with the formulation. Reference is made to the testing method for establishing Foaming Capacity employing equipment that is well known in the art, namely analysis using a Krauss DFA100™ Dynamic Foam Analyzer, which provides a relative measure of achieved foam height upon agitation in a sample having a fixed volume. Foaming Capacity, as used herein relative to foaming on a keratinous substrate, such as facial skin, is based on a scale from low to high, where the scale generally correlates with foaming using a dynamic foam analyzer to provide: low </=220 ml foam), middle (~225-240 ml), to high (>/=250 ml). Thus, the term "high-foaming," with respect to a cleansing composition, refers to a composition that has a high foaming capacity.

As used herein, the term "fail," means all or at least a portion of the composition separates into discrete oil and water phases as evidenced by visual inspection.

In exemplary embodiments, the cleansing composition is not an emulsion. In some embodiments, the cleansing composition is transparent.

In some embodiments, the cleansing composition is a skin cleanser.

In some embodiments, the cleansing composition is a shampoo.

In some embodiments, the cleansing composition is a body wash.

In some embodiments, the cleansing composition is a make-up remover.

Polymeric Thickener

In some embodiments, a cleansing composition includes at least one polymeric thickener. The polymeric thickener preferably is a high-electrolyte polymeric thickener with high stability and high foaming. In some embodiments, the polymeric thickener is an acrylates crosslinking copolymer with electrolytes. In some embodiments, the polymeric thickener is a synthetic acrylates crosspolymer including hydrophilic units and hydrophobic units. In exemplary embodiments, the polymeric thickener is an acrylates/C10-30 alkyl acrylate crosspolymer.

Polymer Thickeners have a high electrolyte property and exhibit a high salt tolerance such that it can thicken in a medium that has high or low amounts of salts, is acidic or basic and includes a wide variety of ingredients. High electrolyte polymers include polymeric repeating units that bear an electrolyte group that may include polycations and polyanions. These groups dissociate in aqueous solutions (water), making the polymers charged. Many biological molecules are polyelectrolytes, such as polypeptides, glycosaminoglycans, and DNA.

Certain polymeric thickeners were tested for certain properties, including electrolyte level, stability at 25° C., stability at 45° C., and foaming ability. The tested formulation ingredients are shown in TABLE 1, wherein the polymer component was varied as shown in TABLE 2.

TABLE 1

| Testing Formulation | | |
|---|---|---|
| INCI name | Formula/ 100 g | Note |
| WATER | Q.S | |
| ACRYLATES/C10-30 ALKYL ACRYLATE CROSSPOLYMER | 1.2 | Polymer Thickener: Experiment in Table 2 |
| GLYCERIN | 10 | |
| SORBITOL | 1 | |
| DISODIUM LAURETH SULFOSUCCINATE (and) SODIUM LAURYL SULFOACETATE | 20 | Anionic Surfactants: Experiment; in Table 3 |
| SODIUM C14-16 OLEFIN SULFONATE | 8 | |
| ISOHEXADECANE | 20 | Oil/Ester (Oil Phase) |
| *HELIANTHUS ANNUUS* (SUNFLOWER) SEED OIL | 10 | Oil/Ester (Oil Phase) |
| HYDROXYACETOPHENONE | 0.5 | Preservative agent |
| CAPRYLYL GLYCOL | 0.3 | Preservative agent |
| TOTAL | 100 | |

The results are summarized in TABLE 2

TABLE 2

| Polymeric thickener Properties | | | | | |
|---|---|---|---|---|---|
| INCI Name | Trade Name | Electrolyte Level | Stability 25° C. | Stability 45° C. | Foaming |
| ACRYLATES/C10-30 ALKYL ACRYLATE CROSSPOLYMER | TEGO CARBOMER 841 SER | High | pass 3 month | pass 3 month | High |
| ACRYLATES/C10-30 ALKYL ACRYLATE CROSSPOLYMER | CARBOPOL ULTREZ 20 POLYMER | High | pass 2 month | pass 2 month | High |
| Hydroxyethyl Cellulose | NATROSOL 250 HHR | No | Fail 4 week | Fail 1 week | Low |
| Hydroxypropyl Methylcellulose | METHOCEL K 15 M PREMIUM | No | Fail 3 week | Fail 1 week | Low |
| Acrylates/Steareth-20 Methacrylate Copolymer | ACULYN ™ 22 | No | Fail 4 week | Fail 1 week | Low |

TABLE 2-continued

Polymeric thickener Properties

| INCI Name | Trade Name | Electrolyte Level | Stability 25° C. | Stability 45° C. | Foaming |
|---|---|---|---|---|---|
| PEG 120 Methyl Glucose Trioleate (and) Propanediol | Glucamate ™ VLT thickener | No | Fail 3 week | Fail 1 week | Low |
| Acrylates/Beheneth 25 Methacrylate Copolymer | Novethix ™ L 10 emulsion polymer | No | Fail 3 week | Fail 1 week | Low |
| XANTHAN GUM | KELTROL CG | No | Fail 4 week | Fail 1 week | Low |
| CARBOMER | CARBOPOL 980 POLYMER | Low | Fail 4 week | Fail 1 week | Low |
| CARBOMER | CARBOPOL 981 POLYMER | Low | Fail 4 week | Fail 1 week | Low |
| ACRYLATES/C10-30 ALKYL ACRYLATE CROSSPOLYMER | CARBOPOL ULTREZ 21 POLYMER | Middle | Fail 6 week | Fail 3 week | Low |
| ACRYLATES COPOLYMER | ARBOPOL AQUA SF-1 POLYMER | Middle | Fail 6 week | Fail 3 week | Low |

As shown in Table 2, the acrylates/C10-30 alkyl acrylate crosspolymer forms that include Tego Carbomer 841 Ser and Carbopol Ultrez 20 Polymer demonstrated desired properties of stability at 45° C. for at least three months and high foaming.

Accordingly, in at least some embodiments, the composition according to the disclosure includes acrylates/C10-30 alkyl acrylate crosspolymer, in particular the high-electrolyte forms supplied that include Tego Carbomer 841 Ser or AQUPEC SERK 300C, or Carbopol Ultrez 20 Polymer, and combinations thereof.

According to the disclosure, other suitable high electrolyte polymers that can be used to provide the cleansing composition may be selected from Polyacrylate Crosspolymer-6 (SepiMax™ Zen), Rheocare® XGN (Xanthan Gum WITH high electrolyte property vs. normal Xanthan Gum).

In at least some embodiments, the composition according to the disclosure excludes one or more polymeric thickeners that are not high-electrolyte thickeners. And more particularly according to such embodiments, the composition excludes hydroxyethyl cellulose, hydroxypropyl methylcellulose, acrylates/steareth-20 methacrylate copolymer, PEG 120 methyl glucose trioleate (and) propanediol, acrylates/beheneth 25 methacrylate copolymer, xanthan gum, carbomer, carbomer, and acrylates/C10-30 alkyl acrylate crosspolymer that do not have high-electrolyte content.

In the various embodiments, the polymeric thickener is present in a cleansing composition, by weight, in an amount in the range of at least 0.1%, or about 0.1% to about 10%, or up to 10%, or about 0.1% to about 1%, or about 1% to about 5%, or about 5% to about 10%, or any value, range, or sub-range therebetween. One of ordinary skill in the art, however, will appreciate that other ranges are within the scope of the invention.

Thus, one or more polymeric thickener is present by weight, based on the total weight of the composition, from about, 0.1, 0.2, 0.3, 0.4, 0.5, 0.6, 0.7, 0.8, 0.9, 11, 2, 3, 4, 5, 6, 7, 8, 9 to about 10 percent, including increments and ranges therein and there between.

Surfactants

In some embodiments, a cleansing composition includes at least one surfactant. In some embodiments, the surfactant is an anionic surfactant. The anionic surfactant preferably is high stability and high foaming. Appropriate anionic surfactants may include, but are not limited to, disodium laureth sulfosuccinate (and) sodium lauryl sulfoacetate, sodium lauroyl sarcosinate, or sodium C14-16 olefin sulfonate.

Certain surfactants were tested for certain properties, including stability at 45° C. and foaming ability. The test formulation is shown in Table 1. The results are summarized in TABLE 3.

TABLE 3

Surfactant Properties

| NAME | CLASS | STABILITY 45° C. | FOAMING |
|---|---|---|---|
| DISODIUM LAURETH SULFOSUCCINATE (and) SODIUM LAURYL SULFOACETATE | Anionic | pass 3 month | High |
| SODIUM LAUROYL SARCOSINATE | Anionic | pass 3 month | High |
| SODIUM C14-16 OLEFIN SULFONATE | Anionic | pass 3 month | High |
| SODIUM COCOYL GLYCINATE | Anionic | Fail 2 week | LOW |
| DECYL GLUCOSIDE | Anionic | Fail 2 week | LOW |
| COCO-BETAINE | Nonionic | Fail 2 week | LOW |
| Cocamidopropyl Betaine | Nonionic | Fail 2 week | LOW |
| Behentrimonium Chloride | Cationic | Fail 4 week | None |
| Cocamidopropyl Betaine | Amphoteric | Fail 2 week | Low |
| COCO-BETAINE | Amphoteric | Fail 2 week | Low |

As shown in TABLE 3, the anionic surfactants disodium laureth sulfosuccinate (and) sodium lauryl sulfoacetate, sodium lauroyl sarcosinate, and sodium C14-16 olefin sulfonate demonstrated desired properties of stability at 45° C. for at least three months and high foaming. Accordingly, in at least some embodiments, the composition according to the disclosure includes one or more of the anionic surfactants selected from the group consisting of disodium laureth sulfosuccinate (and) sodium lauryl sulfoacetate, and sodium lauroyl sarcosinate.

According to the disclosure, other suitable surfactants that can be used to provide the cleansing composition may be selected from Sodium Methyl Lauroyl Taurate, Sodium Cocoyl Alaninate, Sodium Cocoyl Isethionate, and cocamidopropyl hydroxysultaine, and combinations thereof.

In at least some embodiments, the composition according to the disclosure excludes one or more of nonionic, cationic or amphoteric surfactants. And more particularly according to such embodiments, the composition excludes coco-betaine, cocamidopropyl betaine, behentrimonium chloride, cocamidopropyl betaine, coco-betaine or any combination thereof. Further, in at least some embodiments, the composition according to the disclosure comprises an anionic surfactant that excludes each of sodium cocoyl glycinate, and decyl glucoside.

In some embodiments, the surfactant is present in a cleansing composition, by weight, in an amount in the range of at least 1%, or about 1% to about 50%, or up to 50%, or about 1% to about 5%, or about 5% to about 10%, or about 10% to about 30%, or about 30% to about 50%, or any value, range, or sub-range therebetween. One of ordinary skill in the art, however, will appreciate that other ranges are within the scope of the invention.

Thus, any water is present, by weight, based on the total weight of the composition, from about 1, 2, 3, 4, 5, 6, 7, 8, 9, 10, 11, 12, 13, 14, 15, 16, 17, 18, 19, 20, 21, 22, 23, 23, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

In some embodiments, the anionic surfactant is not a sulfate and the cleansing composition is essentially free of emulsifiers, including emulsifiers/surfactants that contain sulfates. Some specific but non-limiting examples of emulsifiers that are lacking from the cleansing composition includes surfactants with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; sorbitan; mono- and di-C8-C20 fatty acids; polyoxyethylene sorbitan; alkyl polyglycosides and saccharide fatty amides (e.g. methyl gluconamides); alkyl ether sulfate and sulfonates; alkyl sulfates and sulfonates; alkylbenzene sulfonates; alkyl and dialkyl sulfosuccinates; C8-C20 acyl isethionates; C8-C20 alkyl ether phosphates; alkylethercarboxylate. Some specific emulsifiers that are lacking from the cleansing composition include PEG-100 Stearate; PEG-20 Stearate and other esters of Poly(Ethylene Glycol); Sucrose Stearate and other emulsifiers based on sugar esters; Glyceryl Stearate and other glycerol esters; Disodium Ethylene Dicocamide PEG-15 Disulfate; Sodium Steroyl Glutamate and other fatty amides; Steareth-100 and other fatty ethers.

In some embodiments, the surfactant is an anionic sulfate surfactant and the cleansing composition is essentially free of salt. Referring again to Table 1, the represented formulation was tested for the effects of salt on stability of the viscosity and foaming. Salt (NaCl) content was varied in a range from 0.1% salt, 0.2% salt, 0.4% salt and up to 4% salt. There was no effect on the viscosity or the phase stability of the composition, and there was no adverse effect on the foaming.

Without being bound by theory, it is believed that with the combination of the polymeric thickener with electrolytes and micelle of the anionic surfactants, the polymer volume decreases, allowing hydrophobic groups to get closer. This acts as pseudo-crosslinking point, leading to a synergistic thickening, increasing the viscosity of the cleansing composition. This creates a cleansing composition having a very high viscosity as a gel.

Water-Based Solvents

A cleansing composition includes at least one solvent comprising at least water.

Water

In the various embodiments, water is present in a cleansing composition, by weight, in an amount from at least 20%, or about 20% to about 50%, or up to 50%, or about 20% to about 30%, or about 30% to about 40%, or about 40% to about 50%, or any value, range, or sub-range therebetween. One of ordinary skill in the art, however, will appreciate that other ranges are within the scope of the invention.

Thus, any water is present, by weight, based on the total weight of the composition, from about 20, 21, 22, 23, 23, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

Water-Soluble Solvents

In accordance with some embodiments, the cleansing composition may include at least one water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90% in water under these conditions. Non-limiting examples of water-soluble solvents include, for example, glycerin, alcohols (for example, C1-C30, C1-C15, C1-C10, or C1-C4 alcohols), organic solvents, polyols, glycols, or mixtures thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylene glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or mixtures thereof.

In some cases, a water-soluble solvent may be selected from the group consisting of one or more glycols, $C_{1-4}$ alcohols, glycerin, or mixtures thereof.

In accordance with the various embodiments total amount of the at least one water-soluble solvent, when present, may vary, is from about 0.5% to about 25%, or from about 0.5% to about 20%, or from about 1% to about 20%, or from about 1% to about 10%, or from about 2% to about 5% or any suitable combination, sub-combination, range, or sub-range thereof by weight, based on the weight of the composition. One of ordinary skill in the art, however, will appreciate that other ranges are within the scope of the invention.

Thus, any one water-soluble solvent, when present, is present, by weight, based on the total weight of the composition, from about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24 to about 25 weight percent, including increments and ranges therein and there between.

It will be appreciated by a skilled artisan that any non-water solvents are present only to the extent and in amounts that do not materially adversely affect the basic and novel characteristic(s) of the claimed disclosure. Thus, in some embodiments that include preservatives, such preservatives will not materially adversely affect the cleansing composition forming a stable gel.

Oils

A cleansing composition includes at least one oil. As used herein, oil refers to any nonpolar compound that is a liquid at 25° C. and is hydrophobic and lipophilic. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa (10-3 to 300 mmHg). The term "non-volatile oil" relates to oil which remains on the skin or the keratin fiber, at room temperature and atmospheric pressure, for at least several hours and which in particular has a vapor pressure of less than 10-3 mmHg (0.13 Pa).

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

The cleansing composition may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Other examples of silicone oils that may be mentioned include volatile linear or cyclic silicone oils, especially those with a viscosity 8 centistokes (8×106 m2/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The cleansing composition may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The cleansing composition may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the composition may include a synthetic oil selected from the group consisting of hydrogenated polyisobutene and hydrogenated polydecene. A hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from C4 to C24, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 40 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ÿ 10, for instance Purcellin oil (cetearyl octanoate), isopropyl myristate, isopropyl palmitate, C12-C15 alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear C12-C13 alkyl) tartrates, such as those sold under the name Cosmacol ETI® by Enichem Augusta Industriale, and also di(linear C14-C15 alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

Hydrocarbon-based oils may be glyceride triesters and in particular to caprylic/capric acid triglycerides, synthetic esters and in particular isononyl isononanoate, oleyl erucate, C12-C15 alkyl benzoate, 2-ethylphenyl benzoate and fatty alcohols, such as octyldodecanol. As volatile hydrocarbon-based oils, mention is made of hydrocarbon-based oils containing from 8 to 16 carbon atoms and in particular of branched C8-C16 alkanes, such as C8-C16 isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C C8-C16 esters, and isohexyl neopentanoate.

In some particular embodiments, the cleansing composition may comprise one or more oils such as from those described herein above, and from oils that may be selected from branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some particular embodiments, suitable liquid alkanes that may be used according to the disclosure include hydrocarbon-based oils containing from 8 to 16 carbon atoms, and especially branched C8-C16 alkanes such as C8-C16 isoalkanes.

In some embodiments, the at least one oil comprises one or more of isohexadecane, C15-19 alkane, isododecane, undecane, tridecane and combinations thereof. In some embodiments, the at least one oil comprises isohexadecane.

In some particular embodiments, the cleansing composition may comprise one or more oils selected from polar emollients selected from esters, triglycerides, ethers, carbonates, alcohols, oils, butters, fatty acids, and their combinations thereof. In various embodiments, the polar emollients may be selected from those with a molecular weight of 400 g/mol or less. More, generally, the polar emollient may have a molecular weight in the range from about 50 g/mol to about 350 g/mol.

In some embodiments, suitable polar emollients that may be used according to the disclosure include those derived from C12-050 fatty acids, preferably C16-C22 saturated fatty acids, and monohydric alcohols. In some embodiments, such esters may be chosen from isopropyl myristate, methyl palmitate, isopropyl laurate, isopropyl palmitate, ethylhexyl palmitate, ethylhexyl laurate, ethylhexyl oleate, ethylhexyl isononanoate, myristyl myristate, 2-ethylhexyl caprate/caprylate (or octyl caprate/caprylate), 2-ethylhexyl palmitate, isostearyl neopentanoate, isononyl isononanoate, hexyl laurate, esters of lactic acid and of fatty alcohols comprising 12 or 13 carbon atoms, dicaprylyl carbonate and their mixtures.

In some embodiments, the at least one oil comprises one of isopropyl myristate, dicaprylyl ether, ethylhexyl palmitate, isopropyl palmitate, cetearyl ethylhexanoate, isononyl isononanoate, isopropyl isostearate, diisopropyl sebacate, coco caprylate/caprate, diisopropyl adipate, and combinations thereof. In some particular embodiments the at least one lipophilic emollient comprises isopropyl myristate.

In some particular embodiments, as exemplified herein, appropriate oils and esters may include, but are not limited to, *Helianthus annuus* (sunflower) seed oil, isohexadecane, isopropyl myristate, ethylhexyl palmitate, sorbitan oleate or other certain hydrocarbons, fatty acids, or esters. In some other embodiments, appropriate oils may include, but are not limited to, castor oil, coconut oil, palm oil, argan oil, jojoba oil, and combinations thereof. In some other embodiments, appropriate esters may include, but are not limited to, C15-19 alkane, neopentyl glycol diethyl hexanoate, cetyl ethylhexanoate, isostearyl hydroxystearate, isodecyl neopentanoate, triisostearyl trilinoleate, triisostearyl citrate, and combinations thereof.

In some embodiments, the oil or ester is present in a cleansing composition, by weight, in an amount of at least 0.1%, or about 0.1% to about 40%, or up to 40%, or about 0.1% to about 1%, or about 1% to about 5%, or about 5% to about 20%, or about 20% to about 40%, or about 40% or more, or not more than about 40%, or any value, range, or sub-range therebetween. One of ordinary skill in the art, however, will appreciate that other ranges are within the scope of the invention.

Thus, each of at least one or more oils or a combination thereof in the composition may be present by weight, based on the total weight of the composition, from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 120, 21, 22, 23, 24, 25, 26, 27, 28, 29, 30, 3, 32, 33, 34, 35, 36, 37, 38, 39 to about 40 percent or more, including increments and ranges therein and there between.

Without being bound by theory, it is believed that the pseudo-crosslinking structure discussed above can also provide long term stability to a gel cleansing composition even with high concentrations of oils being present. This feature is surprising and unexpected for a polymeric thickener and an anionic surfactant.

Silicones

In some embodiments, the cleansing composition includes one or more silicones. In some particular embodiments when the cleansing composition is a shampoo, the cleansing composition includes at least one silicone. Nonetheless, in some instances the composition is free or essentially free of silicones. In other words, one or more of the following silicones may be optionally included or optionally excluded from the composition.

Useful silicones include, but are not limited to, polyorganosiloxanes, polyalkylsiloxanes, polyarylsiloxanes, polyalkarylsiloxanes, polyestersiloxanes, polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds and a mixture thereof. Non-limiting examples include divinyldimethicone/dimethicone copolymer, amodimethicone, dimethicone, cyclomethicone (cyclopentasiloxane), trimethyl silyl amodimethicone, polysilicone-11, phenyl trimethicone, trimethyl siloxy silicate, polymethylsilsesquioxane, trimethylsilylamodimethicone, stearoxytrimethylsilane and a mixture thereof.

In some particular embodiments, appropriate silicones may include, but are not limited to, divinyldimethicone/dimethicone copolymer, amodimethicone, trimethylsiloxysilicate, cyclopentasiloxane, caprylyl methicone, phenyl trimethicone, dimethiconol, or a combination thereof.

In some embodiments, the silicones are present in a cleansing composition, by weight, in an amount of at least 0.5%, or about 0.5% to about 1%, or 5%. One of ordinary skill in the art, however, will appreciate that other ranges are within the scope of the invention.

Thus, any one of the one more silicone compounds, if present, is present, by weight, based on the total weight of the composition, from about 0.5, 0.6, 0.7, 0.8, 0.9, to about 1 weight percent, including increments and ranges therein and there between.

Humectant/Hydrating Agent

In accordance with the disclosure, one or more humectants may be present in the composition. In some embodiments, the humectant may comprise one or more of polyols, including, for example, glycerin, glycerol, glycols, such as, caprylyl glycol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers, such as, monopropylene, dipropylene and tripropylene glycol alkyl(C1-C4)ethers, squalane, triacetin, sugars, such as, glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some particular embodiments, as exemplified herein, a suitable humectant comprises glycerin and sorbitol.

In accordance with the various embodiments, the amount of humectant present in the composition can range from about 1% to about 10%, or from about 1% to about 8%, or from about 1% to about 5%, or from about 2% to about 3%, or any suitable combination, sub-combination, range, or sub-range thereof by weight, based on the weight of the composition. One of ordinary skill in the art, however, will appreciate that other ranges are within the scope of the invention. One of ordinary skill in the art, however, will appreciate that other ranges are within the scope of the invention.

Thus, any one of or a combination of humectant, when present, may be present, by weight, based on the total weight of the composition, is from about 1, 2, 3, 4, 5, 6, 7, 8, 9, to about 10 weight percent, including increments and ranges therein and there between.

Preservatives

In accordance with the disclosure, one or more preservatives and/or antimicrobials may be present in the composition. Any preservative commonly used in cosmetic cleansing compositions is an acceptable preservative for the cleansing compositions herein, such as phenoxyethanol, members from the paraben family such as the methyl, ethyl, propyl, butyl or isobutyl parabens, 4-hydroxy benzoic acid, benzoic acid, sorbic acid, dehydroacetic acid, triclosan, benzyl alcohol, chlorophenesin, or salicylic acid, for example. At more concentrated amounts of suitable solvents for optional additives, in particular, suitable solvents for antimicrobials and preservatives, members from the paraben family may be used as a preservative.

In some embodiments, the preservative may comprise one or more of preservatives selected from the group consisting of organic acids, parabens, formaldehyde donors, phenol derivatives, quaternary ammoniums, alcohols, isothiazolinones, and combinations thereof. Preservatives having antibacterial activity are optionally present in the cleansing compositions of the present invention. Examples of organic acid preservatives include, but are not limited to, sodium benzoate, potassium sorbate, benzoic acid and dehydroacetic acid, sorbic acid, and combinations thereof. A preferred organic acid preservative system includes a mixture of sodium benzoate and potassium sorbate. Examples of paraben preservatives include, but are not limited to, alkyl para-hydroxybenzoates, wherein the alkyl radical has from 1, 2, 3, 4, 5 or 6 carbon atoms and for example, from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Examples of formaldehyde donor preservatives include, but are not limited to, 1,3-Dimethylol-5,5-dimethylhydantoin (DMDM hydantoin), imidazolidinyl urea, gluteraldehyde, and combinations thereof. Examples of quaternary ammonium preservatives include, but are not limited to, benzalkonium chloride, methene ammonium chloride, benzethonium chloride, and combinations thereof. Examples of alcohol preservatives include, but are not limited to, ethanol, benzyl alcohol, dichlorobenzyl alcohol, phenoxyethanol, and combinations thereof. Examples of isothiazolone preservatives include, but are not limited to, methylchloroisothiazolinone, methylisothiazolinone, and combinations thereof.

In some particular embodiments, as exemplified herein, appropriate preservatives include, but are not limited to, phenoxyethanol.

In some embodiments, the preservative includes one or more preservatives, the one or combination present at a concentration, by weight of about 0.001% to about 5%, or alternatively about 0.05% to about 2.5% or alternatively about 0.1% to about 2.0%, based upon weight of the composition. One of ordinary skill in the art, however, will appreciate that other ranges are within the scope of the invention.

Thus, any one of or a combination of preservatives, when present, may be present, by weight, based on the total weight of the composition, is from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2, 3, 4, to about 5 weight percent, including increments and ranges therein and there between.

It will be appreciated by a skilled artisan that any preservatives are present only to the extent and in amounts that do not materially adversely affect the basic and novel characteristic(s) of the claimed disclosure. Thus, in some embodiments that include preservatives, such preservatives will not materially adversely affect the cleansing composition forming a stable gel.

Optional Additives

In some embodiments, a cleansing composition includes at least one additive used in the cosmetics field which does not affect the properties of the composition according to the invention, such as, fragrances, pH adjusters (citric acid, sodium chloride; neutralizing or pH-adjusting agents (e.g., triethylamine (TEA) and sodium hydroxide), and combinations thereof), other cosmetically acceptable additives, such as but not limited to, pearlescent agents, silica, and coloring materials; essential oils; fruit extracts, for example, Pyrus Malus (Apple) Fruit Extract, and Aloe Barbadensis Leaf Juice Powder. Although the optional additives are given as examples, it will be appreciated that other optional components compatible with cosmetic applications known in the art may be used.

In accordance with the various embodiments, the amount of one or more additives, alone or in combination, present in the composition can be present in the composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition. One of ordinary skill in the art, however, will appreciate that other ranges are within the scope of the invention.

Thus, any one or a combination of additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Although the optional additives are given as examples, it will be appreciated that other optional components compatible with cosmetic applications known in the art may be used that are suitable. It will be appreciated by a skilled artisan that any optional additives are present only to the extent and in amounts that do not materially adversely affect the basic and novel characteristic(s) of the claimed disclosure. Thus, in some embodiments that include optional additives, such optional additives will not materially adversely affect the cleansing composition forming a stable gel.

EXAMPLES

The following examples are intended to further illustrate the present disclosure. They are not intended to limit the disclosure in any way. Unless otherwise indicated, all parts are by weight.

Compositions

Comparative Example 1 was based on a cleanser product that included a polymeric thickener but lacked an anionic surfactant. TABLE 4 lists the ingredients and their amounts in weight percentage in Comparative Example 1.

TABLE 4

First Comparative Composition

| INGREDIENT | COMPARATIVE 1 |
| --- | --- |
| ACRYLATES/C10-30 ALKYL ACRYLATE CROSSPOLYMER | 0.50 |
| STYRENE/ACRYLATES COPOLYMER (and) COCO-GLUCOSIDE | 0.5 |
| COCO-BETAINE | 10 |
| GLYCERYL STEARATE (and) PEG-100 STEARATE | 2.0 |
| PPG-5-CETETH-20 | 0.50 |
| SODIUM COCOYL ISETHIONATE | 2.00 |
| SODIUM METHYL COCOYL TAURATE (and) SODIUM CHLORIDE (and) COCONUT ACID | 15.00 |
| WATER | QS |
| GLYCERIN | 5.00 |
| CAPRYLYL GLYCOL | 0.30 |
| CHELATOR | ~0.1 |
| PRESERVATIVE | ~1 |

Comparative Example 2 included an anionic surfactant but lacked a polymeric thickener with a high electrolyte activity. TABLE 5 lists the ingredients and their amounts in weight percentage in Comparative Example 2.

TABLE 5

Second Comparative Composition

| INGREDIENT | COMPARATIVE 2 |
| --- | --- |
| ACRYLATES/BEHENETH-25 METHACRYLATE COPOLYMER | 2.00 |
| COCAMIDOPROPYL BETAINE | 8 |
| DIETHYLHEXYL SODIUM SULFOSUCCINATE | 6 |
| WATER | QS |
| HUMECTANT | 2.00 |
| CAPRYLYL GLYCOL | 0.30 |
| *HELIANTHUS ANNUUS* (SUNFLOWER) SEED OIL | 20.00 |
| ETHYLHEXYL PALMITATE | 20.00 |
| HYDROXYACETOPHENONE | 0.50 |
| SODIUM HYDROXIDE | 0.10 |
| PRESERVATIVE | 0.50 |
| FRAGRANCE | 0.20 |

Five inventive compositions were formed that included a polymeric thickener and an anionic surfactant. TABLE 6 lists the ingredients and their amounts in weight percentage in Inventive Example 1 and Inventive Example 2.

TABLE 6

Inventive Compositions 1-2

| INCI US | INVENTIVE 1 | INVENTIVE 2 |
|---|---|---|
| ACRYLATES/C10-30 ALKYL ACRYLATE CROSSPOLYMER | 0.70 | 1.20 |
| DISODIUM LAURETH SULFOSUCCINATE (and) SODIUM LAURYL SULFOACETATE | 20.00 | 20.00 |
| SODIUM C14-16 OLEFIN SULFONATE | 0 | 3.2 |
| DECYL GLUCOSIDE | 5.00 | 0.00 |
| POLYSORBATE 20 | 0.50 | 0.50 |
| WATER | QS | QS |
| HUMECTANT | ~6 | ~6 |
| ETHYLHEXYL PALMITATE | 5.00 | 7.50 |
| HELIANTHUS ANNUUS (SUNFLOWER) SEED OIL | 10.00 | 15.00 |
| ISOPROPYL MYRISTATE | 5.00 | 7.50 |
| SORBITAN OLEATE | 0.00 | 0.50 |
| PRESERVATIVE | <1 | <1 |

TABLE 7 lists the ingredients and their amounts in weight percentage in Inventive Example 3, and Comparative Example 3 and Comparative Example 4. These examples differed from Inventive Examples 1 and 2 primarily in their relative amounts of water and oils, where Comparative 3 has a polymer that lacks a high electrolyte feature and Comparative 4 lacks an anionic surfactant.

TABLE 7

Inventive Composition 3 and Comparative Compositions 3 and 4

| INCI US | INVEN-TIVE 3 | COMPARA-TIVE 3 | COMPARA-TIVE 4 |
|---|---|---|---|
| ACRYLATES/C10-30 ALKYL ACRYLATE CROSSPOLYMER | 1.0 | 0 | 1.20 |
| CARBOMER | 0 | 1 | 0 |
| DISODIUM LAURETH SULFOSUCCINATE (and) SODIUM LAURYL SULFOACETATE | 20.00 | 20.00 | 20.00 |
| COCAMIDOPROPYL BETAINE | 0 | 0 | 30 |
| SODIUM C14-16 OLEFIN SULFONATE | 3.2 | 3.2 | 0 |
| POLYSORBATE 20 | 0.50 | 0.50 | 0.50 |
| WATER | QS | QS | QS |
| HUMECTANT | ~11 | ~11 | ~11 |
| CAPRYLYL GLYCOL | 0.30 | 0.30 | 0.30 |
| HELIANTHUS ANNUUS (SUNFLOWER) SEED OIL | 10 | 10.00 | 10.00 |
| ISOHEXADECANE | 20.00 | 20 | 20.00 |
| SORBITAN OLEATE | 1.00 | 1.00 | 1.00 |
| HYDROXYACETOPHE-NONE | 0.50 | 0.50 | 0.50 |

Inventive and Comparative compositions were evaluated for foaming and viscosity properties. TABLE 8 provides results of Foaming Capacity and the Viscosity for various tested formulations (Foaming Capacity references the scale described herein above).

TABLE 8

Comparison of Comparative and Inventive Compositions

| FLA | POLYMERIC THICKENER | HIGH ELECTRO-LYTE | ANIONIC SURFACTANT | High % Of Oil Or Ester | VISCOSITY Cps (Spindles 3) | STABILITY |
|---|---|---|---|---|---|---|
| Comparative 1 | YES | NO | YES | NO | ~12,000 | Pass 3 months |
| Comparative 2 | YES | NO | YES | YES | ~20,000 | Phase Separate by 3 weeks |
| Inventive 1 | YES | Yes | YES | YES | ~18,000 | Pass 3 months No separate |
| Inventive 2 | YES | Yes | YES | YES | ~19,000 | Pass 3 months No separate |
| Inventive 3 | YES | YES | YES | YES | ~20,000 | Pass 3 months No separate |
| Comparative 3 | YES | NO | YES | YES | ~11,000 | Phase Separate by 1 weeks |
| Comparative 4 | YES | YES | NO | YES | ~9,000 | Phase Separate by 2 weeks |

Referring to TABLE 8, it is evident that only the inventive composition(s) that include each of the high electrolyte polymeric thickener and anionic surfactant demonstrate both high viscosity with passing stability. This result is unexpected insofar as typical makeup removal formulations that include high amounts of oils and silicones and lack emulsifiers do not typically perform well with foaming and viscosity due to the effects of the oils on surface tension which can reduce or prevent foaming of a composition and which tend to reduce the viscosity of a composition. The instant inventive composition provides high foaming with high and stable viscosity. Comparative 1 includes thickener and surfactant with no oil so it is predictably stable and viscous, but in contrast, Comparative 2 that includes oil without an anionic surfactant phase separates (fails stability test). Comparative examples 3 and 4 differ from Inventive 3 in that they lack one or the other of a high electrolyte polymer and an anionic surfactant in the presence of high oil, and thus both fail stability test and Comparative 4 which lacks the anionic surfactant also has a low viscosity.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The articles "a" and "an", as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The examples serve to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A cleansing composition comprising:
   at least one polymeric thickener having a high electrolyte property; and
   at least one anionic surfactant;
   wherein the cleansing composition is essentially free of sulfates;
   wherein the cleansing composition is essentially free of emulsifiers; and
   wherein the cleansing composition is a gel having a viscosity greater than 25,000 cps.

2. The cleansing composition of claim 1, wherein the at least one polymeric thickener comprises an acrylates crosslinking copolymer.

3. The cleansing composition of claim 2, wherein the at least one polymeric thickener is present in an amount of 0.1 wt % to 10 wt % of the cleansing composition.

4. The cleansing composition of claim 1, wherein the at least one polymeric thickener comprises acrylates/C10-30 alkyl acrylate crosspolymer.

5. The cleansing composition of claim 1, wherein the at least one anionic surfactant is present in an amount of 1 wt % to 50 wt % of the cleansing composition.

6. The cleansing composition of claim 1, wherein the at least one anionic surfactant is selected from the group consisting of disodium laureth sulfosuccinate (and) sodium lauryl sulfoacetate, sodium lauroyl sarcosinate, and sodium C14-16 olefin sulfonate.

7. The cleansing composition of claim 1 further comprising oil in an amount of 0.1 wt % to 40 wt % of the cleansing composition.

8. The cleansing composition of claim 1, wherein the cleansing composition is stable for at least 3 months at 45° C.

9. A cleansing composition comprising:
   at least one polymeric thickener having a high electrolyte property; and
   at least one anionic sulfate surfactant;
   wherein the cleansing composition is essentially free of salt; and
   wherein the cleansing composition is a gel having a viscosity greater than 25,000 cps.

10. The cleansing composition of claim 9, wherein the at least one polymeric thickener comprises an acrylates crosslinking copolymer.

11. The cleansing composition of claim 10, wherein the at least one polymeric thickener is present in an amount of 0.1 wt % to 10 wt % of the cleansing composition.

12. The cleansing composition of claim 9, wherein the at least one polymeric thickener comprises acrylates/C10-30 alkyl acrylate crosspolymer.

13. The cleansing composition of claim 9, wherein the at least one anionic sulfate surfactant is present in an amount of 1 wt % to 50 wt % of the cleansing composition.

14. The cleansing composition of claim 9 further comprising oil in an amount of 0.1 wt % to 40 wt % of the cleansing composition.

15. The cleansing composition of claim 9, wherein the cleansing composition is stable for at least 3 months at 45° C.

* * * * *